(12) United States Patent
Nabeshima et al.

(10) Patent No.: US 10,871,422 B2
(45) Date of Patent: Dec. 22, 2020

(54) APPARATUS AND METHOD FOR TESTING STRENGTH AND DURABILITY OF WEARABLE MOTION ASSISTANCE DEVICE

(71) Applicant: CYBERDYNE INC., Tsukuba (JP)

(72) Inventors: Kota Nabeshima, Ibaraki (JP);
Kazunori Ogami, Ibaraki (JP);
Nobuyoshi Murakami, Ibaraki (JP)

(73) Assignee: CYBERDYNE INC., Tsukuba (JP)

( * ) Notice: Subject to any disclaimer, the term of this patent is extended or adjusted under 35 U.S.C. 154(b) by 30 days.

(21) Appl. No.: 16/470,100

(22) PCT Filed: Dec. 13, 2017

(86) PCT No.: PCT/JP2017/044800
§ 371 (c)(1),
(2) Date: Jun. 14, 2019

(87) PCT Pub. No.: WO2018/110614
PCT Pub. Date: Jun. 21, 2018

(65) Prior Publication Data
US 2019/0316991 A1    Oct. 17, 2019

(30) Foreign Application Priority Data

Dec. 14, 2016   (JP) .................................. 2016-242777

(51) Int. Cl.
*G01M 99/00*       (2011.01)
*A61B 17/17*       (2006.01)
(Continued)

(52) U.S. Cl.
CPC ....... *G01M 99/007* (2013.01); *A61B 17/1764* (2013.01); *A61F 2/4684* (2013.01);
(Continued)

(58) Field of Classification Search
CPC ... G01M 99/007; G01M 7/08; A61B 17/1764; A61F 2/4684; A61F 2002/7695;
(Continued)

(56) References Cited

FOREIGN PATENT DOCUMENTS

| DE | 202005010466 U1 | 9/2005 |
|---|---|---|
| JP | 2014147636 A | 8/2014 |

OTHER PUBLICATIONS

Nabeshima, C., et al., Strength Testing Machines for Wearable Walking Assistant Robots Based on Risk Assessment of Robot Suit HAL, 2012 IEEE International Conference on Robotics and Automation, RiverCentre, Saint Paul, Minnesota, May 14-18, 2012, pp. 2743-2748.

(Continued)

*Primary Examiner* — Jonathan M Dunlap
(74) *Attorney, Agent, or Firm* — Procopio, Cory, Hargreaves & Savitch LLP (57) ABSTRACT

A testing apparatus and testing method capable of efficiently evaluating the strength and durability of a lower-limb-type wearable motion assistance device without being affected by the gravity are implemented. Regarding the testing apparatus for evaluating the strength and durability by repeatedly applying an impact force to the lower-limb-type wearable motion assistance device, when a piston rod is excited at predetermined stroke length and operating speed in a state where a dummy doll wears the wearable motion assistance device, a reciprocable area of a stage relative to an impinging surface of a base is adjusted to make a measured value of a load cell exceed a predetermined reference value.

14 Claims, 10 Drawing Sheets

(51) Int. Cl.
  *A61F 2/46* (2006.01)
  *A61H 1/02* (2006.01)
  *G01M 7/08* (2006.01)
  *A61F 2/76* (2006.01)
  *G01L 5/00* (2006.01)
  *G01N 3/56* (2006.01)
  *G01N 3/34* (2006.01)
  *G01N 3/30* (2006.01)

(52) U.S. Cl.
  CPC ........... *A61H 1/024* (2013.01); *A61H 1/0262* (2013.01); *G01M 7/08* (2013.01); *A61F 2002/7695* (2013.01); *A61H 1/0237* (2013.01); *A61H 2201/165* (2013.01); *A61H 2205/10* (2013.01); *G01L 5/0052* (2013.01); *G01N 3/30* (2013.01); *G01N 3/34* (2013.01); *G01N 3/56* (2013.01)

(58) Field of Classification Search
  CPC .... A61H 1/024; A61H 1/0262; A61H 1/0237; A61H 2205/10; A61H 2201/165; G01L 5/0052; G01N 3/56; G01N 3/34; G01N 3/30
  See application file for complete search history.

(56) References Cited

OTHER PUBLICATIONS

International Search Report for related PCT App No. PCT/JP2017/044800 dated Mar. 20, 2018, 7 pgs.
Extended European Search Report (EESR) directed to the EP counterpart application No. 17880678.2, dated Aug. 4, 2020, Total 8 pages.

APPARATUS AND METHOD FOR TESTING STRENGTH AND DURABILITY OF WEARABLE MOTION ASSISTANCE DEVICE

CROSS-REFERENCE TO RELATED APPLICATIONS

This application is a U.S. National Stage entry of PCT Application No. PCT/JP2017/044800 filed Dec. 13, 2017, which claims priority to Japanese Patent Application No. 2016-242777, filed Dec. 14, 2016, the contents of which are incorporated herein by reference.

TECHNICAL FIELD

The present invention is suited for use in a testing apparatus and testing method for evaluating the strength and durability of, for example, a lower-limb-type wearable motion assistance device, which assists walking motion, with respect to an impact load generated successively while a wearer is walking.

BACKGROUND ART

Safety evaluation of a wearable motion assistance device requires exhaustive verification including tests. Regarding the evaluation of electrical safety, verification methods established according to existing international safety standards can be applied. On the other hand, regarding a mechanical safety evaluation method, any verification methods suited for the wearable motion assistance device including methods for evaluating the strength and durability have not been established.

A mechanical structure of a lower-limb-type wearable motion assistance device is similar to that of an orthosis to wear for the purpose of walking such as an ankle orthosis. However, any standard testing method for evaluating the durability of an orthosis against impacts successively caused during walking has not been established yet. This may be because an impact force generated by landing is dispersed non-uniformly to a wearer and the structure.

On the other hand, regarding an artificial leg with a knee joint, a durability test is specified by the International Safety Standards ISO 10328. This ISO 10328 requires a test to apply a repetitive compression load of 1 to 4 [Hz] to the artificial leg at a position where a bending moment is applied to an angle limitation of the joint. When a wearer with body weight of 80 [kg] is assumed, compatibility is judged based on whether there is any deformation or damage caused after applying a compressive force of 1,180 to 1,230 [N] 3,000,000 times.

In a case of a mechanism for walking by supporting the entire body weight of a wearer, the testing condition of ISO 10328 seems reasonable. This testing condition of ISO 10328 corresponds to estimation of a foot sole load caused by landing during walking as 1.6 times the body weight. It is known that the foot sole load when walking on the flat land is approximately 1.3 times the body weight and the foot sole load when going down stairs is approximately 1.5 times the body weight. Therefore, the numeric value of 1.6 times the body weight is reasonable as the testing condition.

In a case of the lower-limb-type wearable motion assistance device, the load is dispersed to the wearer's body and the structure of the wearable motion assistance device and, therefore, it is well expected that the strength and durability required for the wearable motion assistance device itself may be less than the strength and durability required for an orthosis. However, the problem is that a ratio of the load dispersion between the human body and the wearable motion assistance device is not obvious and a simple compressive force test cannot be applied.

Intuitively, the test seemed possible if it were possible to make a dummy doll that imitates the structure of the human body wear the lower-limb-type wearable motion assistance device and walk. However, it is necessary to make the dummy doll walk stably for a long time in order to carry out this test; and this seemed very difficult considering the current walking technology for humanoid robots.

Figure 10:
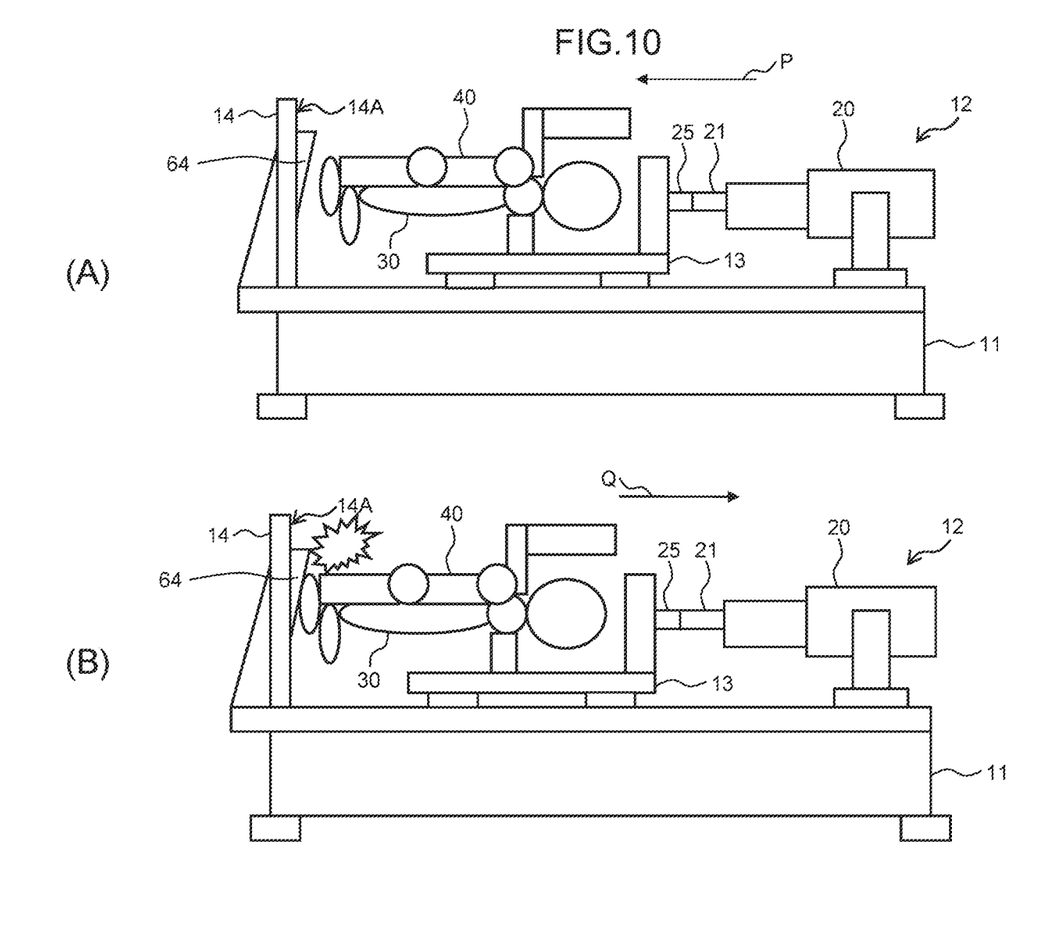
FIG. 10 is a schematic diagram for explaining a testing method for evaluating the strength and durability of the entire configuration of a wearable motion assistance device regarding conventional successive landing.

Accordingly, the inventors of the present application developed a method for testing the strength and durability of the entire wearable motion assistance device by making a dummy doll which imitates a human wear the lower-limb-type wearable motion assistance device and land on the floor successively in an upright condition as illustrated in FIG. 10. Regarding this testing method, the dummy doll is caused to wear the wearable motion assistance device in a manner similar to a normal method. The mass, size, and a major degree of freedom of each part of the dummy doll imitate those of an intended wearer.

According to this testing method, the dummy doll is lifted up by using a winch and then is made to fall down freely by gravity. When a dummy doll which is specified to ensure reproducibility is used, a test parameter would be only a lift-up height. This lift-up height is adjusted while monitoring a floor reaction force upon landing on the floor, so that a peak value of the floor reaction force will become a value calculated by multiplying a constant by a sum of the weight of the dummy doll and the weight of the wearable motion assistance device. When the testing condition of ISO 10328 is to be satisfied, adjustments should be made so that the impact force for each one leg becomes 1.6 times the body weight.

Whether this test is successful or not is judged based on whether there is any failure or defect caused after landing on the floor for a specified number of times. The specified number of times is determined according to use frequency and use time during the lifetime of the wearable motion assistance device. When the testing condition of ISO 10328 is to be satisfied, the specified number of times is 3,000,000 times.

CITATION LIST

Non-Patent Literature

NPL 1: Cota Nabeshima, Hiroaki Kawamoto and Yoshiyuki Sankai, "Strength Testing Machines for Wearable Walking Assistant Robots based on Risk Assessment of Robot Suit HAL," ICRA2012, Saint Paul, Minn., USA, May 16, 2012

SUMMARY OF THE INVENTION

Problems to be Solved by the Invention

Meanwhile, since the testing method of successive landing by the above-described free fall utilizes the gravity, problems are caused with respect to the following four points. Specifically speaking, firstly, a test speed cannot be increased; secondly, the impact force may easily vary widely depending on the structure of the dummy doll and changes in the posture of the dummy doll over time; thirdly, measure points of the impact force are not constant and it is difficult to measure the impact force due to the changes in the posture of the dummy doll over time; and fourthly, when dummy dolls of different sizes are to be manufactured, it is difficult to make their mass and sizes match each other appropriately at the same time.

Therefore, it is desirable that the gravity should not be used for a method for testing the strength and durability of the entire structure of the lower-limb-type wearable motion assistance device with respect to successive landing.

The present invention was devised in consideration of the above-described circumstances and aims at proposing a testing apparatus and testing method for efficiently evaluating the strength and durability of the lower-limb-type wearable motion assistance device without using the gravity.

Means to Solve the Problems

In order to solve the above-described problems, a testing apparatus for evaluating strength and durability by repeatedly applying an impact force to a lower-limb-type wearable motion assistance device is provided according to the present invention, wherein the testing apparatus includes: a base at one end of which an impinging surface is formed along a vertical direction; a vibration exciter that is secured at another end of the base and causes reciprocating motion of a piston rod by driving an actuator to excite the piston rod in a horizontal and straight linear direction; a stage that is connected to a tip of the piston rod and can be moved freely slidably on the base integrally with the piston rod; a dummy doll that is secured and retained on the stage and partially imitates at least a lower back part and legs of a human body; and a load cell that is provided on a tip of the piston rod or the impinging surface and measures, via the stage, distortion caused by application of a load on a foot part of the dummy doll, wherein when the piston rod is excited at predetermined stroke length and operating speed in a state where the dummy doll wears the wearable motion assistance device, a reciprocable area of the stage relative to the impinging surface of the base is adjusted to make a measured value of the load cell exceed a predetermined reference value.

As a result, the testing apparatus for evaluating the strength and durability does not use the gravity unlike the case of successive landing by free falls, the test speed can be set freely, and it becomes easier to stably measure the impact force generated on the foot parts. Therefore, the strength and durability of the wearable motion assistance device can be evaluated with respect to the impacts generated successively while the wearer is walking.

Furthermore, the present invention further includes: a monitoring unit that monitors the measured value of the load cell; and an adjustment unit that automatically adjusts the reciprocable area of the stage relative to the impinging surface of the base on the basis of a monitoring result of the monitoring unit. As a result, it is possible to avoid the trouble of manual adjustments.

Furthermore, according to the present invention, the dummy doll has a support to be secured and retained on the stage, a leg guard rod corresponding to a length to the foot part is secured and coupled to one side of the support and a back guard rod corresponding to a length to the lower back part is secured and coupled to another side of the support; and wherein artificial body imitating parts, each of which imitates the human body, are formed on the leg guard rod and the back guard rod at sites corresponding to a plurality of cuffs provided on the wearable motion assistance device.

It becomes possible to relatively easily manufacture the structure which can hardly cause considerable variations of the impacts, by making the dummy doll with the minimum necessary structure for repeatedly application of the impacts.

Furthermore, according to the present invention, the artificial body imitating parts are: artificial foot parts, each of which imitates the foot part of the human body; artificial lower leg parts, each of which imitates a lower leg part; artificial femoral parts, each of which imitates a femoral part; and an artificial lower back part which imitates the lower back part. The configuration of the dummy doll can be simplified by providing only the parts corresponding the respective cuffs of the wearable motion assistance device which is an object to wear.

Furthermore, according to the present invention, each leg guard rod of the dummy doll is inclined relative to, and secured to, the support in such a direction and at such an angle as to imitate a desired resting state in a kinetic chain of the human body during walking; and an offset flat member is attached to the impinging surface of the base so that only the artificial foot part formed on the leg guard rod inclined relative to the support enters into contact with the offset flat member. Accordingly, it becomes possible to perform an impact force test repeatedly so that an impact force from the impinging surface will be generated on the foot sole surfaces of the artificial foot parts in such a direction and at such an angle as to imitate the desired resting state in the kinetic chain of the human body during actual walking.

Furthermore, according to the present invention, a jig of a predetermined shape that defines an inclination direction and inclination angle of a contact site of each artificial foot part is attached to the impinging surface of the base. Accordingly, when a person has their own habit (tilting of the foot soles) in a landing state while walking, the impact force test can be performed repeatedly so that the impact force from the impinging surface will be generated on the foot sole surfaces of the artificial foot parts in accordance with such habit.

Furthermore, according to the present invention, a jig of a predetermined shape that imitates a desired road surface condition is attached to the impinging surface of the base. Accordingly, the impact force test can be performed repeatedly so that the impact force from the impinging surface will be generated on the foot sole surfaces of the artificial foot parts in accordance with desired various road surface conditions.

Furthermore, provided according to the present invention is a testing method for evaluating strength and durability by repeatedly applying an impact force to a lower-limb-type wearable motion assistance device, wherein the following are included: a base at one end of which an impinging surface is formed along a vertical direction; a vibration exciter that is secured at another end of the base and causes reciprocating motion of a piston rod by driving an actuator to excite the piston rod in a horizontal and straight linear direction; a stage that is connected to a tip of the piston rod and can be moved freely slidably on the base integrally with the piston rod; and a dummy doll that is secured and retained on the stage and partially imitates at least a lower back part and legs of a human body; and wherein when the piston rod is excited at predetermined stroke length and operating speed in a state where the dummy doll wears the wearable motion assistance device, a reciprocable area of the stage relative to the impinging surface of the base is adjusted to make a measured value of distortion caused by application of a load on a foot part of the dummy doll, which is measured by a load cell provided on a tip of the piston rod or the impinging surface, exceed a predetermined reference value.

As a result, the testing method will not be affected by the gravity unlike the case of successive landing by free falls, so that the test speed can be set freely, and it becomes easier to measure the impact force stably. Therefore, the strength and durability of the wearable motion assistance device can be evaluated with respect to the impacts generated successively while the wearer is walking.

Advantageous Effects of the Invention

According to the present invention, a testing apparatus and testing method capable of efficiently evaluating the strength and durability of the wearable motion assistance device with respect to impacts, which are caused successively while a wearer is walking, without being affected by the gravity.

DESCRIPTION OF EMBODIMENTS

An embodiment of the present invention will be described below in detail with reference to the drawings.

Figure 1:
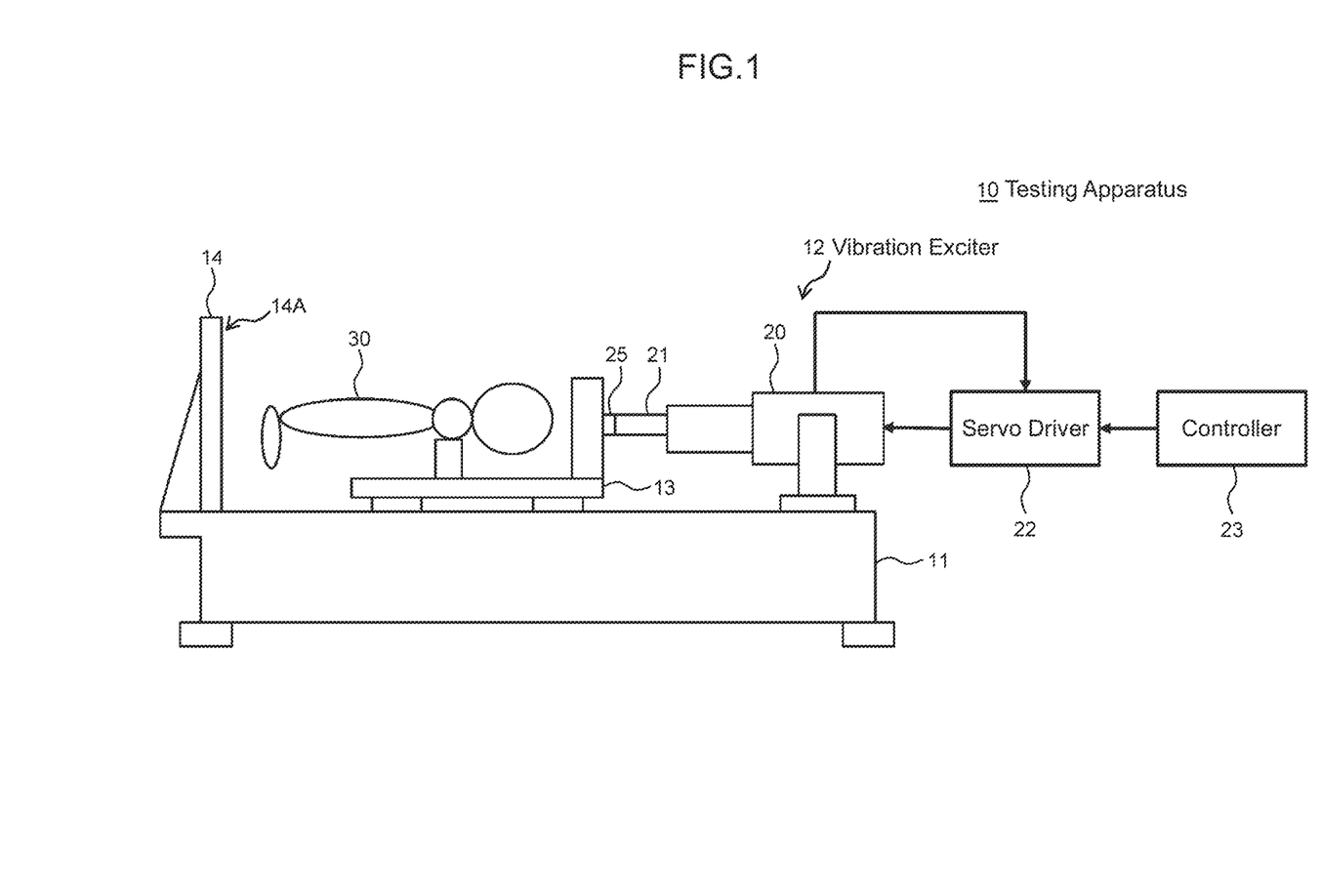
FIG. 1 is a schematic side view illustrating an overall configuration of a testing apparatus according to an embodiment of the present invention.

(1) Configuration of Testing Apparatus for Evaluating Strength and Durability of Wearable Motion Assistance Device FIG. 1 illustrates a testing apparatus 10 according to this embodiment and is configured of a base 11 installed on a floor surface, a vibration exciter 12 secured on the base 11, and a stage 13 that can be moved freely slidably on the base 11 according to an excitation action by the vibration exciter 12.

With the testing apparatus 10, an impact receiver 14 with an impinging surface 14A formed along the vertical direction is formed at one end of the base 11 and integrally with the base 11; and a vibration exciter 12 is secured on the other end of the base 11 and opposite to the impinging surface 14A of the impact receiver 14.

The vibration exciter 12 consists of an electric-servo-type vibration exciter (for example, a product name "NJ-SERVO" by SHIMADZU CORPORATION) and is configured of: an electric actuator 20 in which a piston rod 21 performs reciprocating motion in a straight linear direction as it is driven by an AC servo motor; a servo driver 22 that controls the electric actuator 20; and a controller 23 that delivers a command signal to the servo driver 22.

The electric actuator 20 has an encoder (position detector) built therein for detecting a rotation amount of the AC servo motor and sends a feedback signal from the encoder to the servo driver 22. The servo driver 22 compares the actual position, speed, and torque value of the AC servo motor based on the feedback signal with the respective values based on the original command signal from the controller and thereby detects errors between those values and then corrects the action of the AC servo motor on a real-time basis (closed control) by using such errors.

The stage 13 connected to the tip of the piston rod 21 of the electric actuator 20 is provided between the impact receiver 14 and the vibration exciter 12 on the base 11 so that the stage 13 can move integrally with the piston rod 21 and freely slidably on the base 11. A dummy doll 30 which imitates a part of a human body is secured and retained on the top of the stage 13. This dummy doll 30 can be secured and retained on the stage 13 and can be removed from the stage 13 as necessary.

Furthermore, a load cell 25 is built in the tip of the piston rod 21 in the electric actuator 20 for the vibration exciter 12; and when the dummy doll 30 hits the impinging surface 14A of the impact receiver 14 on the base 11 as described later with reference to FIG. 3, it is designed to measure distortion, which is caused by a load applied on foot parts of the dummy doll 30, via the stage 13.

With the testing apparatus 10 as described above, a vibration load can be applied successively to the dummy doll 30, which is secured and retained on the stage 13, by having the electric actuator 20 excite the stage 13 installed in a manner reciprocable via a bearing (not shown) on the top face of the base 11.

Figure 2:
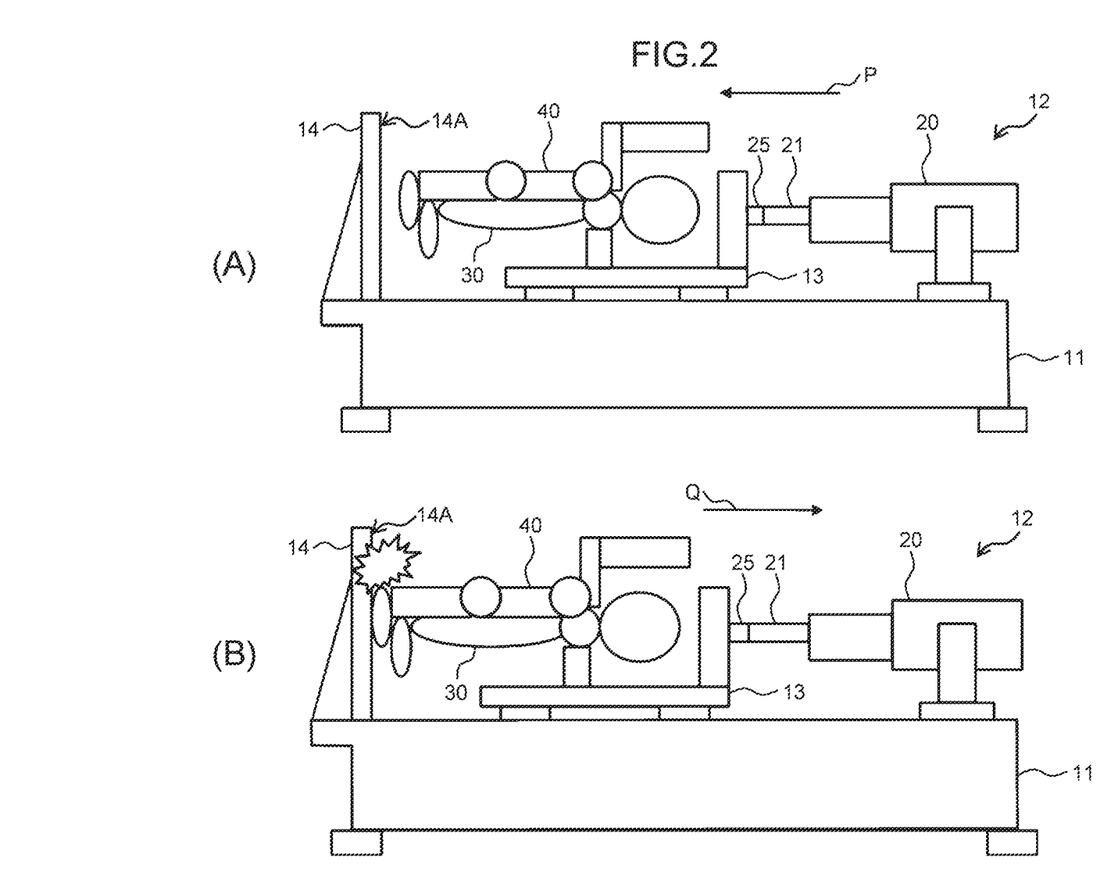
FIG. 2 is a schematic side view for explaining a repeating test according to an embodiment of the invention.

Practically, with the testing apparatus 10 as illustrated in FIG. 2A and FIG. 2B, the electric actuator 20 of the vibration exciter 12 is driven to cause the piston rod 21 perform reciprocating motion in a direction indicated with arrow P or a direction indicated with arrow Q in a state where the dummy doll 30 wears a lower-limb-type wearable motion assistance device 40 (FIG. 4), so that the dummy doll 30 which slides in the straight linear direction integrally with the stage 13, together with the wearable motion assistance device 40, is made to repeatedly hit the impinging surface 14A of the impact receiver 14 and then the durability of the wearable motion assistance device 40 is evaluated.

(2) Configuration of Dummy Doll According to this Embodiment

Figure 3:
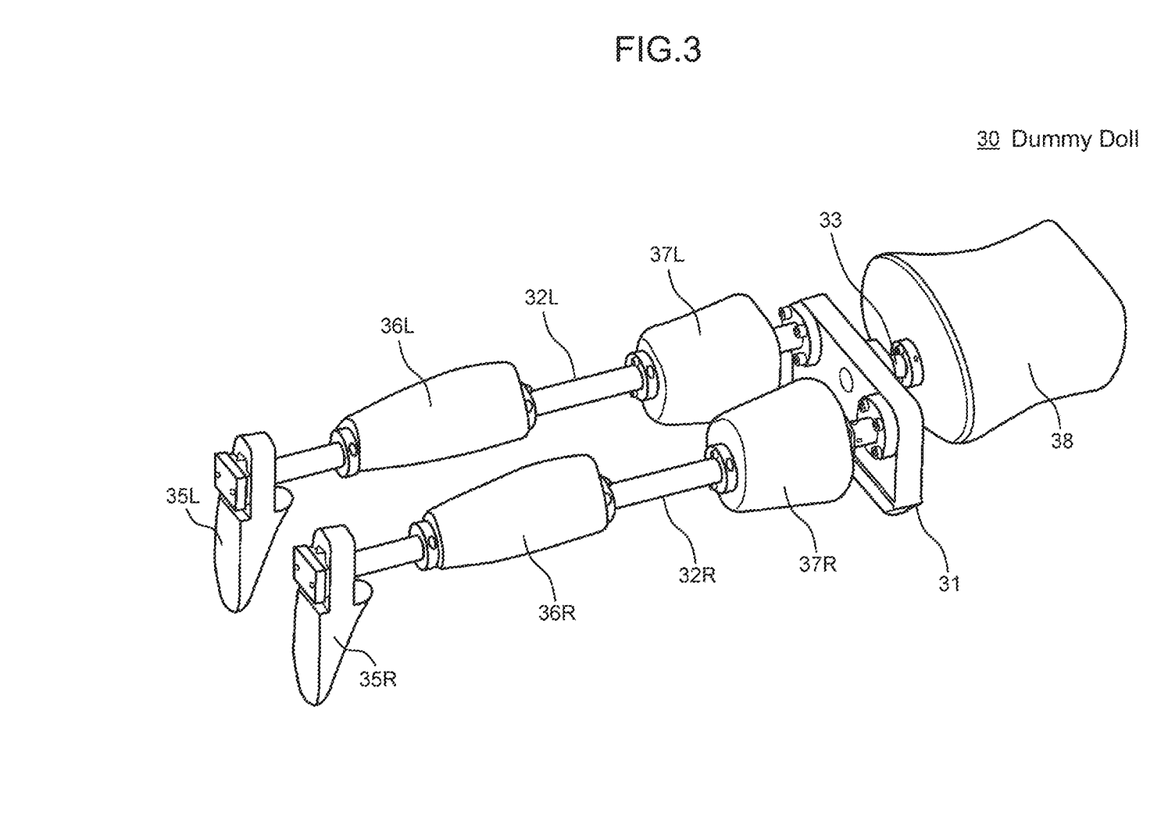
FIG. 3 is a perspective view illustrating the configuration of a dummy doll according to the embodiment.

The dummy doll 30 according to this embodiment has the structure that partly imitates lower limbs of a human body as illustrated in FIG. 3, wherein a support 31 corresponding to a crotch part is secured and retained on the stage 13 in such a manner that the support 31 can be freely attached to or detached from the stage 13.

A pair of leg guard rods 32L, 32R corresponding to the length to both foot parts is secured and coupled to one side of the support 31 of the dummy doll 30, while a back guard rod 33 corresponding to the length to a lower back part is secured and coupled to the other side of the support 31.

Artificial body imitating parts 36 to 38 which respectively imitate a human body are formed on the pair of leg guard rods 32L, 32R and the back guard rod 33 of the dummy doll 30 at sites corresponding to a plurality of cuffs (not shown) provided on the wearable motion assistance device 40. The artificial body imitating parts 36 to 38 are: artificial foot parts 35L, 35R which respectively imitate a pair of foot parts of the human body; artificial lower leg parts 36L, 36R which respectively imitate a pair of lower leg parts; artificial femoral parts 37L, 37R which respectively imitate a pair of femoral parts; and an artificial lower back part 38 which imitates a lower back part.

Figure 4:
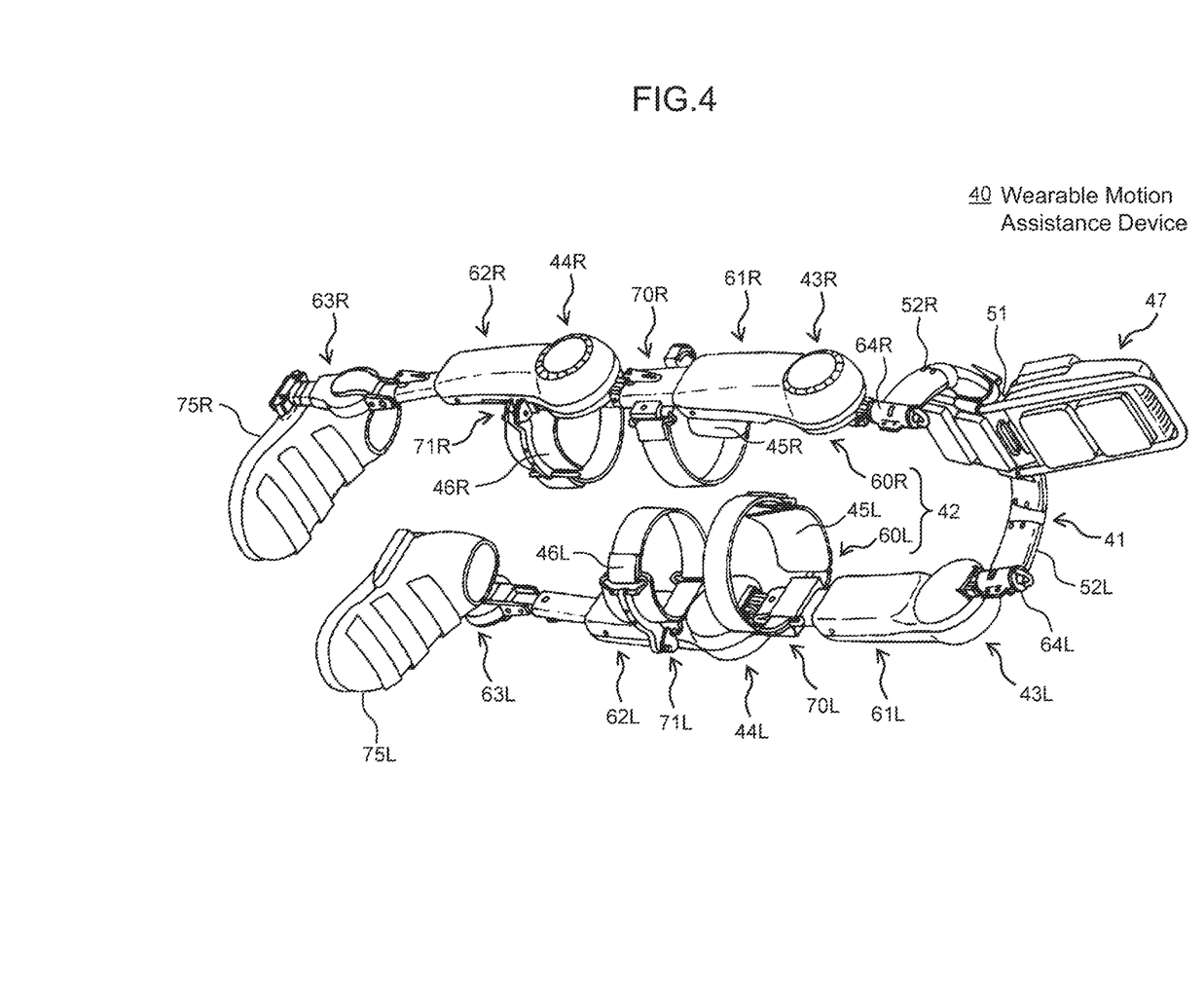
FIG. 4 is a perspective view illustrating the configuration of a wearable motion assistance device according to the embodiment.

(3) Configuration of Wearable Motion Assistance Device According to this Embodiment The lower-limb-type wearable motion assistance device 40 according to this embodiment includes: a lower-back frame 41 to be mounted on the lower back of a wearer (the dummy doll 30 which imitates a human body in this embodiment); a lower limb frame 42 to be mounted on the wearer's lower limbs; a plurality of drive units 43L, 43R, 44L, 44R provided on the lower limb frame 42 corresponding to the wearer's joints; cuffs 45L, 45R, 46L, 46R serving as assisting power acting members attached to the lower limb frame 42 so as to cause the power of the drive units 43L, 43R, 44L, 44R act on the wearer from their front or their back; a control unit (not shown) that controls the drive units 43L, 43R, 44L, 44R according to signals attributable to the wearer's motions; a back-side unit 47 equipped with the control unit; and an operation unit (not shown) used by a helper.

The lower-back frame 41: is a substantially C-shaped member, as viewed from above, which is open forward and can receive the wearer's lower back and surround it from its back side to its right and left lateral sides; and includes a rear lower-back frame part 51 located behind the wearer, and a left lower-back frame part 52L and a right lower-back frame part 52R which bend from both ends of the rear lower-back frame part 51 and extend forward. The left lower-back frame part 52L and the right lower-back frame part 52R are coupled to the rear lower-back frame part 51 via an opening adjustment mechanism (not shown). Base parts of the left lower-back frame part 52L and the right lower-back frame part 52R are inserted, in a manner slidable from side to side, into the rear lower-back frame part 51 and retained in the rear lower-back frame part 51.

The lower limb frame 42 includes: a right lower-limb frame 60R to be mounted on the wearer's right lower limb; and a left lower-limb frame 60L to be mounted on the wearer's left lower limb. The left lower-limb frame 60L and the right lower-limb frame 60R are formed symmetrically.

The left lower-limb frame 60L includes: a left thigh frame 61L located on the left side of the wearer's left thigh; a left lower leg frame 62L located on the left side of the wearer's left lower leg; and a left leg lower-end frame 63L on which the wearer's left leg underside (or a left-side shoe sole when the wearer wears shoes) is to be placed. The left lower-limb frame 60L is coupled, via a lower-back part connecting mechanism 64L, to the tip part of the left lower-back frame part 52L.

The right lower-limb frame 60R includes: a right thigh frame 61R located on the right side of the wearer's right thigh; a right lower leg frame 62R located on the right side of the wearer's right lower leg; and a right leg lower-end frame 63R on which the wearer's right leg underside (or a right-side shoe sole when the wearer wears shoes) is to be placed. The right lower-limb frame 60R is coupled, via a lower-back part connecting mechanism 64R, to the tip part of the right lower-back frame part 52R.

One cuff 45L, 45R, 46L, 46R is provided on each of the left thigh frame 61L, the right thigh frame 61R, the left lower leg frame 62L, and the right lower leg frame 62R.

The cuffs provided on the left thigh frame 61L and the right thigh frame 61R (hereinafter referred to as the "thigh cuffs") 45L, 45R are supported by thigh cuff support mechanisms 70L, 70R attached to the lower ends of the thigh frame body. The thigh cuff 45L, 45R has a mounting surface bent in an arc shape which can be placed in close contact with, and engage with, the wearer's thigh. A fitting member is attached to the mounting surface of the thigh cuff 45L, 45R so that the thigh cuff 45L, 45R can closely contact the wearer's thigh without any gap between them.

The cuffs provided on the left lower leg frame 62L and the right lower leg frame 62R (hereinafter referred to as the "lower-leg cuffs") 46L, 46R are supported by lower-leg cuff support mechanisms 71L, 71R attached to the upper ends of upper-side elements. The lower-leg cuff 46L, 46R has a mounting surface bent in an arc shape which can be placed in close contact with, and engage with, the wearer's lower leg. A fitting member is attached to the mounting surface of the lower-leg cuff 46L, 46R so that the lower-leg cuff 46L, 46R can closely contact the wearer's lower leg without any gap between them.

When this wearable motion assistance device is to be actually mounted on the dummy doll 30, shoes 75L, 75R are placed on the right and left artificial foot parts 35L, 35R, respectively, the lower-leg cuffs 46L, 46R are mounted on the right and left artificial lower leg parts 36L, 36R, respectively, and the thigh cuffs 45L, 45R are further mounted on the right and left artificial femoral parts 37L, 37R. Then, the shoes and the cuffs are fastened with belts or the like so that these artificial body imitating parts (the artificial foot parts, the artificial lower leg parts, and the artificial femoral parts) are integrated with their corresponding frames.

(4) Testing Method According to this Embodiment

When the testing apparatus 10 drives the electric actuator 20 of the vibration exciter 12 to excite the piston rod 21 at a predetermined stroke length and operating speed in the state where the dummy doll 30 wears the wearable motion assistance device 40, a reciprocable area of the stage 13 relative to the impinging surface 14A of the impact receiver 14 of the base 11 is adjusted so that a measured value of the load cell 25 exceeds a predetermined reference value.

(4-1) Estimation of Foot Sole Impact Force During Walking

The impact force on the foot sole surfaces when the dummy doll 30 is actually made to hit the impinging surface 14A of the impact receiver 14 of the base 11 is estimated from the following point of view.

Generally, the foot sole impact force of a healthy person during walking is said to be 1.2 to 1.3 times their body weight; and some data also shows that when a person walks at a speed of 4.0 [km/h], the foot sole impact force is approximately 1.3 times their body weight. Moreover, since a walking speed for rehabilitation of gait disorder is 2 [km/h] or less, it is reasonable to believe that the actual foot sole impact force would be not more than 1.3 times their own body weight.

However, in this embodiment, the foot sole impact force is estimated by assuming a worst value or higher. A conventional example of a lower limb orthosis intended for use in daily walking is an artificial leg(s) including joint parts. Regarding the strength of the artificial leg including a knee joint and an ankle joint, the standard (ISO 10328) specifies a testing method and conformity standards.

The artificial leg is a tool intended to become a substitute for the body structure and also support the body weight. Accordingly, the load used for testing is large and the number of times of repetitive load to be tested is also large. Examples of load values for an artificial leg durability strength repeating test that is the standard (ISO 10328) are as follows: when a test load condition is to support the body weight of 100 [kg], a repeating test load is 1,280 to 1,330 [N] and the number of times of the repeating test is 3,000,000 [times].

The artificial leg strength test is designed so that the impact force generated on the foot soles by walking is estimated as a value calculated by multiplying the relevant person's body weight by a value equal to 1.6 times the gravity. Specifically, the impact force is estimated as follows: impact force [N]=(body weight)×1.6×9.8 [m$^2$/s].

In a case of the lower-limb-type wearable motion assistance device, the wearer's body weight is supported by their own body and a joint movable range in use is limited naturally. Therefore, it is not reasonable to apply the artificial leg strength test, without any change, to the wearable motion assistance device; however, conditions are set with reference to the above-described formula.

It is assumed that the load caused by the impact force will be approximately 1.6 times the body weight at a maximum. Therefore, acceleration applied to the wearable motion assistance device is defined as 1.6 times the gravity and the impact force generated by the load caused by the body weight and a basic machine weight is defined as a value calculated by multiplying the relevant load by a value equal to 1.6 times the gravity. Specifically, the impact force is defined as follows: impact force [N]=(load)×1.6×9.8 [m2/s].

For example, the impact force imposed on one foot sole surface of the dummy doll when the wearer of the body weight 100 [kg] wears the wearable motion assistance device of 13 [kg] can be estimated as (100 [kg]+13 [kg])×1.6×9.8 [m$^2$/s]≈1,771 [N].

Incidentally, regarding the impact force on the foot soles, a load caused by motion going down stairs is supposed to be more disadvantageous conditions (conditions with higher impact force) than those of the walking motion. According to the results of past experiments, data of a healthy person shows that a peak of the load imposed on their support leg when either starting or stopping the motion going up or down the stairs of 180 [mm] is not more than 1.6 times their body weight.

Accordingly, the testing apparatus 10 performs the impact force test repeatedly in the state where the dummy doll 30 which imitates the structure of the human body wears the wearable motion assistance device 40, so that the impact force generated on the foot sole surfaces of the artificial foot parts 35L, 35R satisfies the above-mentioned relationship when the dummy doll 30 hits the impinging surface 14A of the impact receiver 14 of the base 11.

(4-2) Adjustments of Strokes

Subsequently, the vibration exciter 12 adjusts strokes of the piston rod 21 of the electric actuator 20 so that the following conditions are satisfied: the impact force imposed on the foot sole surfaces of both the artificial foot parts 35L, 35R of the dummy doll 30 is equal to or more than 3,542 [N] (≈2 [feet]×(100 [kg]+13 [kg])×1.6×9.8[m/s$^2$]); the stroke length is 10 [mm]; and the operating speed is 4 [Hz].

Firstly, the dummy doll 30 wearing the wearable motion assistance device 40 is caused to slide together with the stage 13 in a straight linear direction and the foot sole surfaces of both the artificial foot parts 35L, 35R are made to enter into contact with the impinging surface 14A of the impact receiver 14 of the base 11. A measured value of the load cell 25 which is built in the tip of the piston rod 21 is recorded at that position.

Subsequently, while the vibration exciter 12 drives the electric actuator 20 to perform excitation, the position of the stage 13 at the time of collision is manually adjusted so that the measured value of the load cell 25 exceeds the aforementioned estimated value 3,542 [N]. Then, a position which is 10 [mm] of the stroke length away from the above-adjusted position is recorded.

An area between these recorded positions is recognized as the reciprocable area and the value of the load cell 25 is checked by increasing the operating speed for the reciprocating motion of the piston rod 21 from 0.5 [Hz] to 4.0 [Hz] by 0.5 to 1.0 [Hz].

Under this circumstance, rubber components and resin components of the shoe soles deform due to external force at the time of mounting. So, the position of the stage 13 at the time of collision is changed so that the measured value of the load cell 25 becomes equal to or more than 3,542 [N]; and the reciprocable area is changed so that the stroke length becomes 10 [mm].

(4-3) Successive Collision Test

With the testing apparatus 10, after making the dummy doll 30 wear the wearable motion assistance device 40 and adjusting the reciprocable area of the stage 13 with reference to the stroke length of the piston rod 21 of the electric actuator 20 as described above, the controller 23 sets the number of cycles. What a default number of times should be is determined according to the user frequency and use time during life time of the wearable motion assistance device. If the testing condition of ISO 10328 is to be satisfied, the default number of times is set to 3,000,000 times.

Next, while causing the piston rod 21 of the electric actuator 20 to perform the reciprocating motion at a predetermined operating speed, the vibration exciter 12 monitors the peak value of the load cell 25 about once per one to two days and adjusts the reciprocable area of the stage 13 so that the impact force will not fall under 3,542 [N].

The above-described test is performed for the specified repetitive number of times and whether judgment criteria described below are satisfied and the tested device is considered to be successfully acceptable or not is checked and recorded. If the device is recognized as nonacceptable due to failed conformity of the standards in the middle of testing, the number of times of landing and the reason for nonacceptance are recorded and the test is finished. For example, loosened fixing screws may be fastened during the test, but in which cycle of the test the screws were fastened is recorded.

(4-4) Judgment Criteria

When the judgment criteria described below are not satisfied after performing the collision test for the aforementioned number of repetitive times, the tested device is judged to be nonacceptable. The judgment criteria are as follows:

firstly, no components of the wearable motion assistance device have fallen off; secondly, there is no cracks or missing parts in the exterior parts of the device or such damage will not cause unacceptable risk; thirdly, there are no loosened screws for fastening strength members together; fourthly, there is no creaking abnormal noise, hardness to move, or backlashes as compared to before the test when movable parts or an adjustment unit are moved manually; fifthly, the power is turned on (when an electric system is mounted) and the specified test operation is operated properly without any alarm; and sixthly, there is no abnormality in connectors (for example, no connector has loosened, has come off, or has deformed).

(5) Other Embodiments

Incidentally, this embodiment has been described above about the case where the electric actuator 20 is applied as a mechanism for causing the reciprocating motion of the piston rod 21 of the vibration exciter 12; however, the present invention is not limited to this example and a wide variety of drive types such as not only the electric type, but also a hydraulic type or a pneumatic type may be applied as long as the stroke length and the operating speed of the piston rod can be satisfied for practical use.

Furthermore, this embodiment has described the case where the position of the stage 13 is adjusted manually when the strokes of the piston rod 21 in the vibration exciter 12 are adjusted; however, the present invention is not limited to this example and an adjustment unit (not shown) capable of automatically adjusting a slide position may be provided on the stage 13 so that as the servo driver (monitoring unit) 22 monitors the measured value of the load cell, the adjustment unit may automatically adjust the reciprocable area relative to the impinging surface 14A of the base 11 on the basis of the monitoring results.

Furthermore, this embodiment has described the case where the load cell 25 is built in the tip of the piston rod 21 of the electric actuator 20; however, the present invention is not limited to this example and similar measurement effects can be obtained if a load cell (not shown) is mounted at each of the four corners of the impinging surface 14A of the impact receiver 14 and the impinging surface 14A is thereby made to serve as a force plate.

Furthermore, this embodiment has described the case where the dummy doll having the configuration as illustrated in FIG. 3 is applied; however, the present invention is not limited to this example and dummy dolls with a wide variety of structures may be applied as long as each one of such dummy dolls can be secured or retained on the stage 13 and has artificial body imitating parts corresponding to the respective cuffs of the wearable motion assistance device 40 which is the object to be evaluated.

Furthermore, this embodiment has described the case where the wearable motion assistance device with the configuration as illustrated in FIG. 4 is applied; however, the present invention is not limited to this example and can be applied to a wide variety of lower-limb-type wearable motion assistance devices with various configurations. Regarding the wearable motion assistance device, not only the two-leg structure, but also a one-leg structure can be applied. In this case, a dummy doll with the structure of only a single leg may be applied accordingly.

Figure 5:
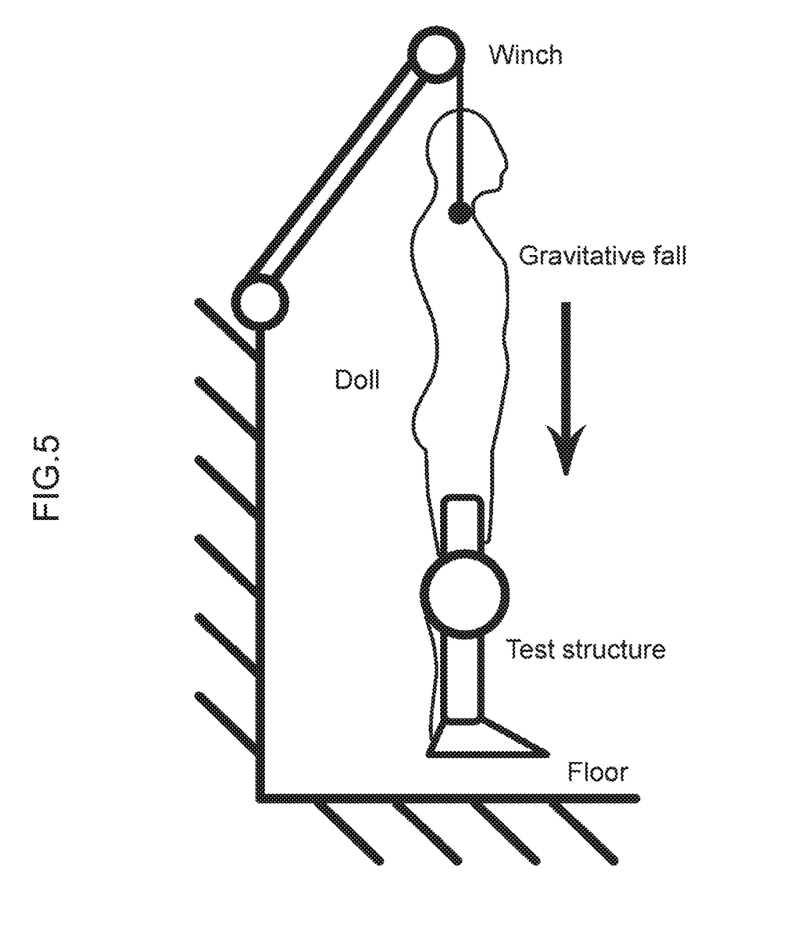
FIG. 5 is a schematic top view illustrating the configuration of a testing apparatus according to another embodiment.
Figure 6:
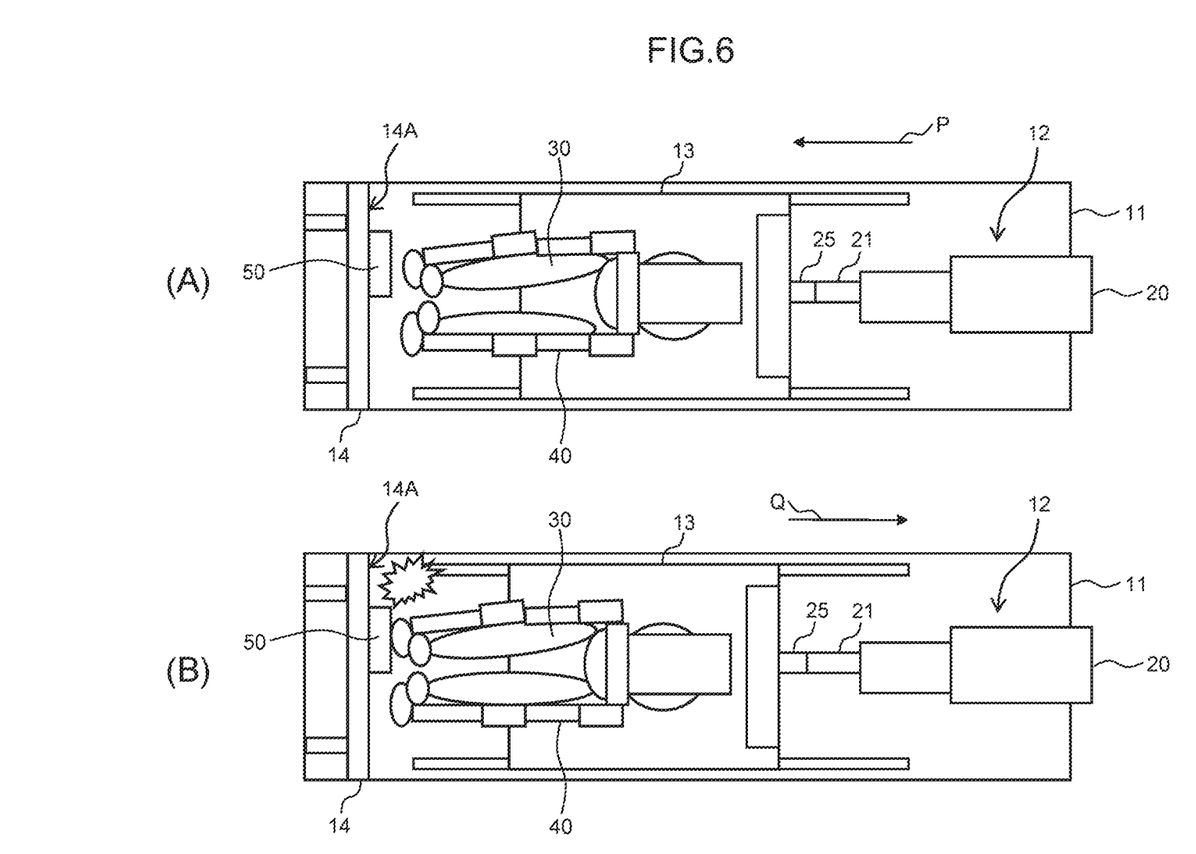
FIG. 6 is a schematic top view illustrating the configuration of a testing apparatus according to another embodiment.

Furthermore, in this embodiment, regarding the dummy doll 30 secured and retained on the stage 13, each leg guard rod 32L, 32R of the dummy doll 30 may be inclined relative to, and secured to, the support 31 in such a direction and at such an angle as to imitate a desired resting state in a kinetic chain of the human body during walking as illustrated in FIG. 5A and FIG. 5B in which the same reference numerals are assigned to parts corresponding to those in FIG. 2A and FIG. 2B.

Specifically speaking, the kinetic chain represents that once some joint is moved, its adjacent joint moves subsequently and a chain of movements happens at various sites. For example, there are two patterns of kinetic chains during walking: a descending kinetic chain that have effects on their pelvis towards their ankle joints; an ascending kinetic chain in which movements of the ankle joints have effects on knee joints, hip joints, and then the pelvis.

Furthermore, the descending kinetic chain is divided into a kinetic chain caused by anteversion of the pelvis and a kinetic chain caused by retroversion of the pelvis. On the other hand, the ascending kinetic chain is divided into a kinetic chain caused by pronation of subtalar joints and a kinetic chain caused by supination of the subtalar joints.

Specifically speaking, regarding the kinetic chain of the descending type caused by the anteversion of the pelvis, when the pelvis tilts forward, the hip joints are flexed, are adducted, and rotate inward, then the knee joints extend, evert, and rotate outward, the lower legs tilt inward and rotate inward, and the subtalar joints pronate. On the other, regarding the kinetic chain of the descending type caused by the retroversion of the pelvis, when the pelvis tilts backward, the hip joints extend, are abducted, and rotate outward, then the knee joints are flexed, invert, and rotate inward, the lower legs tilt outward and rotate outward, and the subtalar joints supinate.

Further specifically, regarding the kinetic chain of the ascending type caused by the pronation of the subtalar joints, when the subtalar joints pronate, the lower legs tilt inward and rotate inward, then the knee joints are flexed, evert, and rotate inward, the hip joints are flexed, are adducted, and rotate inward, and the pelvis rotate forward. On the other hand, regarding the kinetic chain of the ascending type caused by the supination of the subtalar joints, when the subtalar joints supinate, the lower legs tilt outward and rotate outward, then the knee joints extend, invert, and rotate outward, the hip joints extend, are abducted, and rotate outward, and the pelvis rotates backward.

The leg guard rods 32L or 32R of the dummy doll 30 are inclined relative to, and secured to, the support 31 in such a direction and at such an angle as to imitate a resting state for which testing is desired, from among the above-described kinetic chains of the human body during walking.

In accordance with such inclination, an offset flat member 50 of specified size and thickness is mounted on the impinging surface 14A of the impact receiver 14 of the base 11 so that only the artificial foot part 35L or 35R formed on the leg guard rod 32L or 32R which is inclined relative to the support 31 enters into contact with the offset flat member 50.

As a result, when the vibration load is applied successively in the state where the dummy doll 30 wearing the wearable motion assistance device 40 is secured and retained on the stage 13, this durability evaluation testing apparatus 10 can perform the impact force test repeatedly so that the impact force from the impinging surface 14A will be generated on the foot sole surfaces of the artificial foot parts 35L or 35R in such a direction and at such an angle as to imitate the desired resting state from among the kinetic chains of the human body during actual walking.

Furthermore, in this embodiment, jigs 61 to 64 of predetermined shapes which define the inclination direction and the inclination angle of a contact site of each artificial foot part 35L, 35R may be attached to the impinging surface 14A of the impact receiver 14 of the base 11 as illustrated in FIGS. 6A and 6B to FIGS. 9A and 9B in which the same reference numerals are assigned to parts corresponding to those in FIG. 2A and FIG. 2B.

Figure 7:
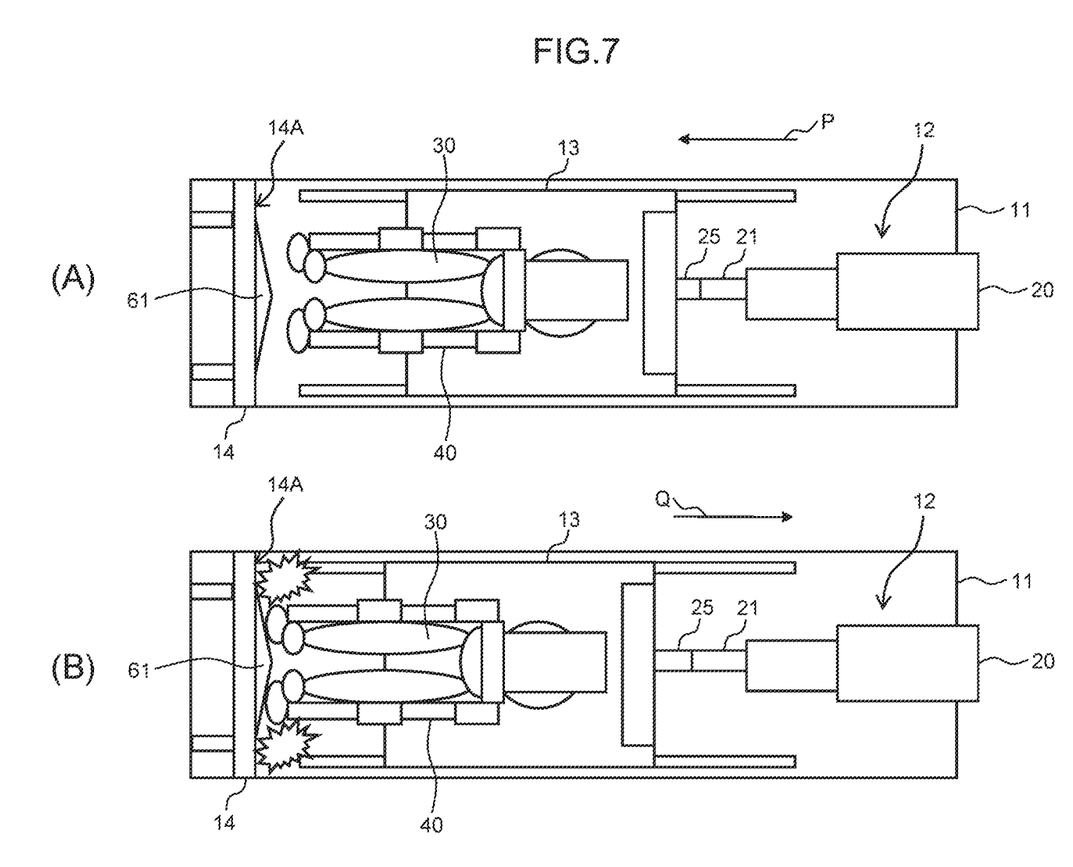
FIG. 7 is a schematic top view illustrating the configuration of a testing apparatus according to another embodiment.

Specifically speaking, the jig 61 having a substantially isosceles triangular cross-sectional shape in a predetermined inclination direction and at a predetermined inclination angle is mounted on the impinging surface 14A of the impact receiver 14 of the base 11 by assuming supinated positions of the subtalar joints so that only the inside of the contact site (corresponding to the foot sole) of each artificial foot part 35L, 35R enters into contact with the jig 61 (FIG. 7A and FIG. 7B).

Figure 8:
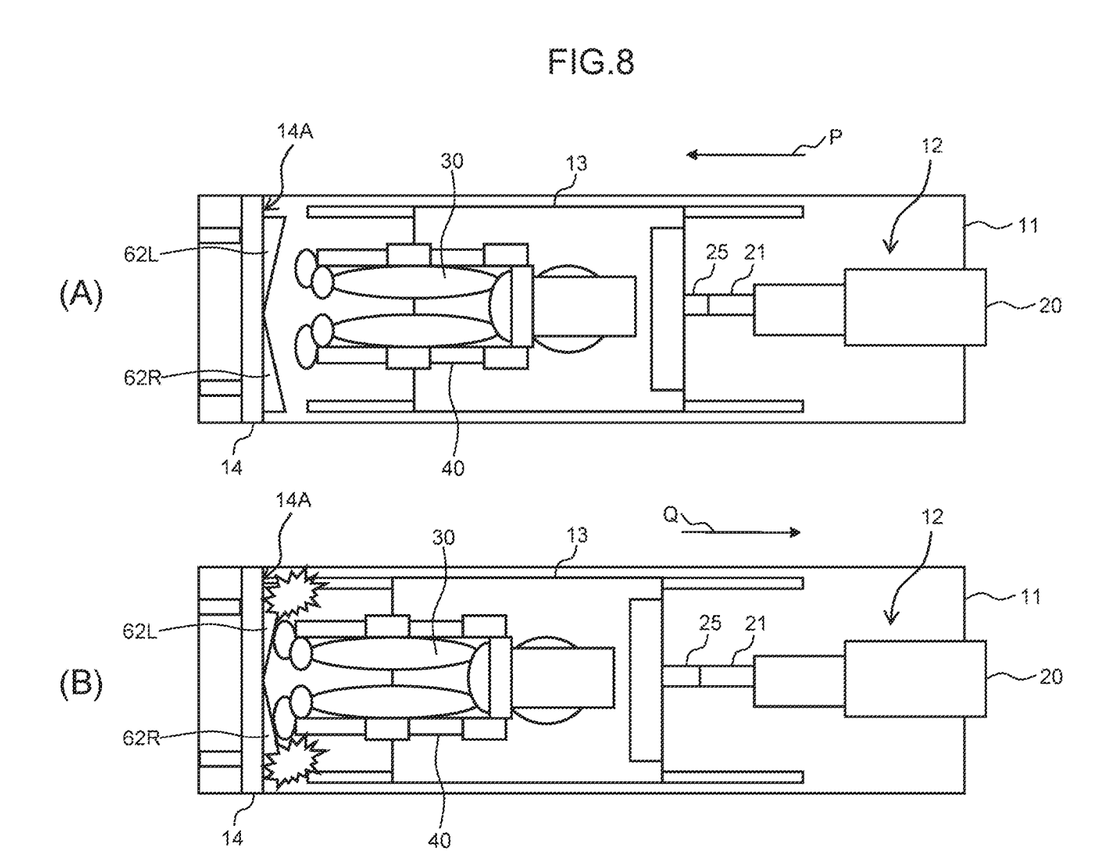
FIG. 8 is a schematic side view illustrating the configuration of a testing apparatus according to another embodiment.

Furthermore, a pair of jigs 62L, 62R having a substantially right-angled triangular cross-sectional shape in a predetermined inclination direction and at a predetermined inclination angle is mounted on the impinging surface 14A of the impact receiver 14 of the base 11 by assuming pronated positions of the subtalar joints so that only the outside of the contact site (corresponding to the foot sole) of each artificial foot part 35L, 35R enters into contact with the jig 62L, 62R (FIG. 8A and FIG. 8B).

Figure 9:
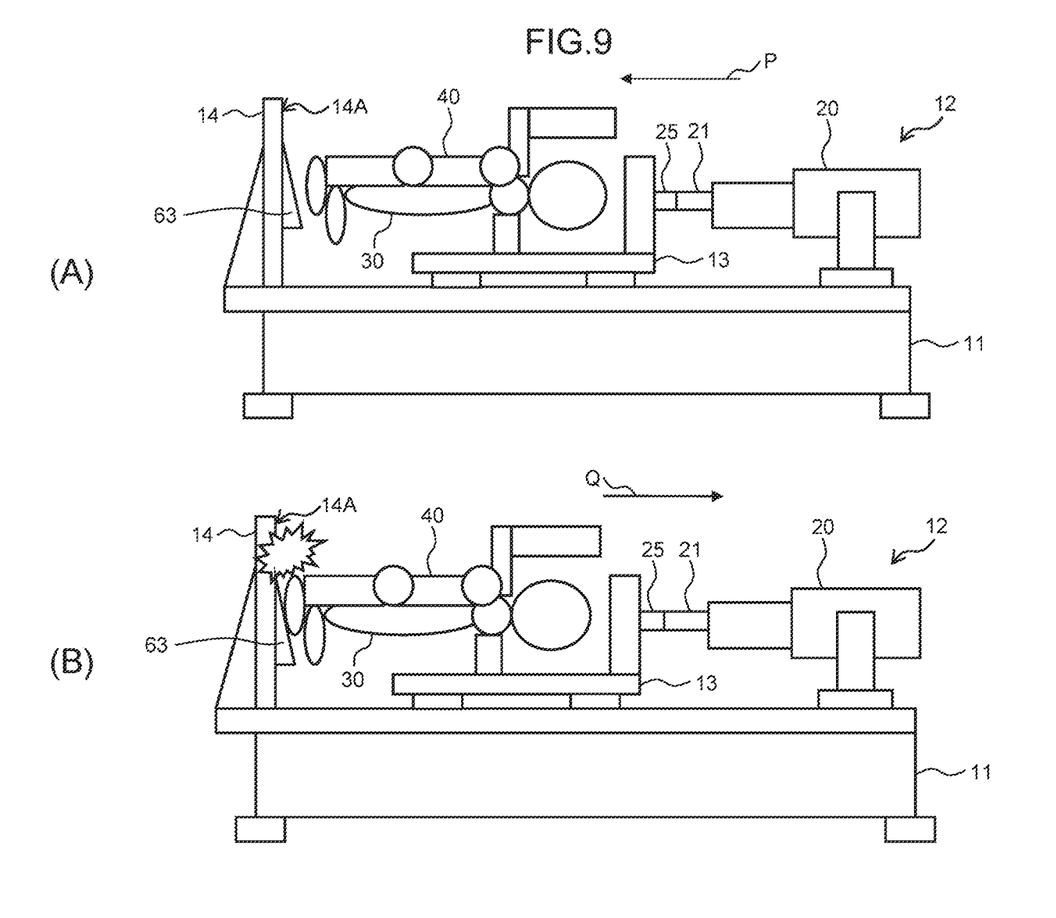
FIG. 9 is a schematic side view illustrating the configuration of a testing apparatus according to another embodiment.

Furthermore, the jig 63 having a substantially right-angled triangular cross-sectional shape in a predetermined inclination direction and at a predetermined inclination angle is mounted on the impinging surface 14A of the impact receiver 14 of the base 11 by assuming dorsiflexed positions of the subtalar joints so that only the rear foot part (heel) of the contact site (corresponding to the foot sole) of each artificial foot part 35L, 35R enters into contact with the jig 63 (or the foot part is bent toward the foot dorsum direction) (FIG. 9A and FIG. 9B).

Furthermore, the jig 64 having a substantially right-angled triangular cross-sectional shape in a predetermined inclination direction and at a predetermined inclination angle is mounted on the impinging surface 14A of the impact receiver 14 of the base 11 by assuming plantarflexed positions of the subtalar joints so that only the front foot part (toes) of the contact site (corresponding to the foot sole) of each artificial foot part 35L, 35R enters into contact with the jig 64 (or the foot part is bent toward the foot bottom direction) (FIG. 10A and FIG. 10B).

Accordingly, when this durability evaluation testing apparatus 10 is used to apply the vibration load successively in the state where the dummy doll 30 wearing the wearable motion assistance device 40 is secured and retained on the stage 13 and if a person has their own habit of a landing state during walking (tilting of the foot soles), the impact force test can be performed repeatedly so that the impact force from the impinging surface 14A will be generated on the foot sole surfaces of the artificial foot parts 35L or 35R in accordance with the habit.

Furthermore, in this embodiment, a jig (not shown) of a predetermined shape which imitates a desired road surface condition (such as a rough road surface or a bumpy road) may be attached to the impinging surface 14A of the impact receiver 14 of the base 11. Also, in this case, the impact force test can be performed repeatedly so that the impact force from the impinging surface 14A will be generated on the foot sole surfaces of the artificial foot parts 35L or 35R in accordance with the road surface condition.

REFERENCE SIGNS LIST 10 testing apparatus
11 base
12 vibration exciter
13 stage
14 impact receiver
14A impinging surface
20 electric actuator
21 piston rod
22 servo driver
23 controller
25 load cell
30 dummy doll
31 support
40 wearable motion assistance device
40 offset flat member
61-64 jigs

The invention claimed is:

1. A testing apparatus for evaluating strength and durability by repeatedly applying an impact force to a lower-limb-type wearable motion assistance device, the testing apparatus comprising:
    a base at one end of which an impinging surface is formed along a vertical direction;
    a vibration exciter that is secured at another end of the base and causes reciprocating motion of a piston rod by driving an actuator to excite the piston rod in a horizontal and straight linear direction;
    a stage that is connected to a tip of the piston rod and can be moved freely slidably on the base integrally with the piston rod;
    a dummy doll that is secured and retained on the stage and partially imitates at least a lower back part and legs of a human body; and
    a load cell that is provided on a tip of the piston rod or the impinging surface and measures, via the stage, distortion caused by application of a load on a foot part of the dummy doll,
    wherein when the piston rod is excited at predetermined stroke length and operating speed in a state where the dummy doll wears the wearable motion assistance device, a reciprocable area of the stage relative to the impinging surface of the base is adjusted to make a measured value of the load cell exceed a predetermined reference value.

2. The testing apparatus for the wearable motion assistance device according to claim 1, further comprising:
    a monitoring unit that monitors the measured value of the load cell; and
    an adjustment unit that automatically adjusts the reciprocable area of the stage relative to the impinging surface of the base on the basis of a monitoring result of the monitoring unit.

3. The testing apparatus for the wearable motion assistance device according to claim 1,
    wherein the dummy doll has a support to be secured and retained on the stage, a leg guard rod corresponding to a length to the foot part is secured and coupled to one side of the support and a back guard rod corresponding to a length to the lower back part is secured and coupled to another side of the support; and
    wherein artificial body imitating parts, each of which imitates the human body, are formed on the leg guard rod and the back guard rod at sites corresponding to a plurality of cuffs provided on the wearable motion assistance device.

4. The testing apparatus for the wearable motion assistance device according to claim 1,
    wherein the artificial body imitating parts are: artificial foot parts, each of which imitates the foot part of the human body; artificial lower leg parts, each of which imitates a lower leg part; artificial femoral parts, each of which imitates a femoral part; and an artificial lower back part which imitates the lower back part.

5. The testing apparatus for the wearable motion assistance device according to claim 1,
wherein each leg guard rod of the dummy doll is inclined relative to, and secured to, the support in such a direction and at such an angle as to imitate a desired resting state in a kinetic chain of the human body during walking; and
wherein an offset flat member is attached to the impinging surface of the base so that only the artificial foot part formed on the leg guard rod inclined relative to the support enters into contact with the offset flat member.

6. The testing apparatus for the wearable motion assistance device according to claim 1,
wherein a jig of a predetermined shape that defines an inclination direction and inclination angle of a contact site of each artificial foot part is attached to the impinging surface of the base.

7. The testing apparatus for the wearable motion assistance device according to claim 1,
wherein a jig of a predetermined shape that imitates a desired road surface condition is attached to the impinging surface of the base.

8. A testing method for evaluating strength and durability by repeatedly applying an impact force to a lower-limb-type wearable motion assistance device,
wherein the following are included: a base at one end of which an impinging surface is formed along a vertical direction; a vibration exciter that is secured at another end of the base and causes reciprocating motion of a piston rod by driving an actuator to excite the piston rod in a horizontal and straight linear direction; a stage that is connected to a tip of the piston rod and can be moved freely slidably on the base integrally with the piston rod; and a dummy doll that is secured and retained on the stage and partially imitates at least a lower back part and legs of a human body; and
wherein when the piston rod is excited at predetermined stroke length and operating speed in a state where the dummy doll wears the wearable motion assistance device, a reciprocable area of the stage relative to the impinging surface of the base is adjusted to make a measured value of distortion caused by application of a load on a foot part of the dummy doll, which is measured by a load cell provided on a tip of the piston rod or the impinging surface, exceed a predetermined reference value.

9. The testing method for the wearable motion assistance device according to claim 8,
wherein the reciprocable area of the stage relative to the impinging surface of the base is automatically adjusted on the basis of a result of monitoring the measured value of the load cell.

10. The testing method for the wearable motion assistance device according to claim 8,
wherein the dummy doll has a support to be secured and retained on the stage, a leg guard rod corresponding to a length to the foot part is secured and coupled to one side of the support and a back guard rod corresponding to a length to the lower back part is secured and coupled to another side of the support; and
wherein artificial body imitating parts, each of which imitates the human body, are formed on the leg guard rod and the back guard rod at sites corresponding to a plurality of cuffs provided on the wearable motion assistance device.

11. The testing method for the wearable motion assistance device according to claim 8,
wherein the artificial body imitating parts are: artificial foot parts, each of which imitates the foot part of the human body; artificial lower leg parts, each of which imitates a lower leg part; artificial femoral parts, each of which imitates a femoral part; and an artificial lower back part which imitates the lower back part.

12. The testing method for the wearable motion assistance device according to claim 8,
wherein each leg guard rod of the dummy doll is inclined relative to, and secured to, the support in such a direction and at such an angle as to imitate a desired resting state in a kinetic chain of the human body during walking; and
wherein an offset flat member is attached to the impinging surface of the base so that only the artificial foot part formed on the leg guard rod inclined relative to the support enters into contact with the offset flat member.

13. The testing method for the wearable motion assistance device according to claim 8,
wherein a jig of a predetermined shape that defines an inclination direction and inclination angle of a contact site of each artificial foot part is attached to the impinging surface of the base.

14. The testing method for the wearable motion assistance device according to claim 8,
wherein a jig of a predetermined shape that imitates a desired road surface condition is attached to the impinging surface of the base.

* * * * *